United States Patent [19]

Ogura

[11] Patent Number: 5,022,749
[45] Date of Patent: Jun. 11, 1991

[54] AUXILIARY INSTRUMENT FOR EXAMINING EYES

[75] Inventor: Nobunori Ogura, Tokyo, Japan
[73] Assignee: Rainbow Optical Laboratory Co., Ltd., Tokyo, Japan
[21] Appl. No.: 375,698
[22] Filed: Jul. 5, 1989
[30] Foreign Application Priority Data May 28, 1988 [JP] Japan .................................. 63-70630

[51] Int. Cl.⁵ .............................................. A61B 3/00
[52] U.S. Cl. .................................................. 351/219
[58] Field of Search .................. 351/205, 219, 160 R, 351/160 H

[56] References Cited

U.S. PATENT DOCUMENTS 4,502,764 3/1985 Riquin ................................. 351/219

*Primary Examiner*—Rodney B. Bovernick
*Attorney, Agent, or Firm*—Cushman, Darby & Cushman

[57] ABSTRACT

An auxiliary instrument to be used for examining an eye, which is effectively used for avoiding the tip portion of an eye-examining instrument from directly contacting with a cornea, and for guiding the tip portion of the eye-examining instrument. This auxiliary instrument comprises a contact lens portion having a spherical bottom surface which is adapted to be fittingly contacted with the surface of the cornea and an examination surface portion which is to be contacted with the tip portion of the eye-examining instrument; and a guide portion projected outward surrounding the examination surface portion. This guide portion may be prepared separately from the contact lens portion.

5 Claims, 2 Drawing Sheets

AUXILIARY INSTRUMENT FOR EXAMINING EYES

BACKGROUND OF THE INVENTION (a). Field of the Invention

This invention relates to an auxiliary instrument which is adapted to be attached to eyes for the examination of eyes.

(b). Description of the Prior Art

In the conventional method of taking a picture of a cornea by using a specula microscope in the examination of the cornea, a cone lens attached to the distal end of the specula microscope is directly contacted with the cornea.

Accordingly, there has been a possibility to injure the cornea due to an excessive pressing locally of the cone-lens of the specula-microscope onto a portion of an ectocornea, or a rubbing of the ectocornea.

Moreover, with the conventional method of taking a picture of a cornea, it is rather difficult to accurately keep the cone-lens at a precise photographing position, so that it is required not only a great deal of skill, but also a long time for taking a picture of the cornea.

Almost the same problems are encountered in using any examining instrument other than the specula-microscope, which has been conventionally operated while contacting the distal end of the instrument to an eye.

Therefore, a development of a device which allows the examination of an eye to be conducted without directly contacting an examining instrument with the eye of a patient has been highly solicited.

SUMMARY OF THE INVENTION

This invention has been made in view of the above-mentioned circumstances, and the main object of this invention is to provide an auxiliary instrument for the examination of eyes, which allows the examination of eyes to be conducted without directly contacting an examining instrument to a cornea, and is useful in guiding the examining instrument to be easily set at an accurate examination position.

In order to achieve above object, this invention provides as a first feature an auxiliary instrument for the examination of eyes which comprises a contact lens portion having a spherical surface which is adapted to be fittingly contacted with a surface of cornea of an eyeball; an examination surface portion formed at a central portion of the contact lens; and a guide portion projected outward surrounding the examination surface portion.

This invention further provides as a second feature an auxiliary instrument for the examination of eyes which comprises a contact lens portion having a spherical surface which is adapted to be fittingly contacted with a surface of cornea of an eyeball; an examination surface portion formed at and protruding outward from a central portion of the contact lens; an overlay lens portion which is adapted to be overlaid on a top surface of the contact lens portion; and a guide portion having an opening formed at the center thereof which is adapted to be fitted with the examination surface portion when the overlaying lens portion is overlaid on the contact lens portion, the guide portion being projected outward around the opening.

In an auxiliary instrument for examination of eyes as proposed by this invention, the inner surface of the contact lens portion is first fittingly contacted with the cornea of a patient, thereby avoiding an examining instrument from being directly contacted with the cornea of the patient.

In addition to that, since the guide portion of the contact lens is so disposed as to surround the outer protruding surface of the examination surface portion, it has become possible to easily guide and set the distal end portion of an examining instrument of contact type at a predetermined examination position of a patient through this guide portion.

DESCRIPTION OF THE PREFERRED EMBODIMENT

This invention will be further explained with reference to preferred embodiments shown in FIGS. 1 to 4.

Figure 1:
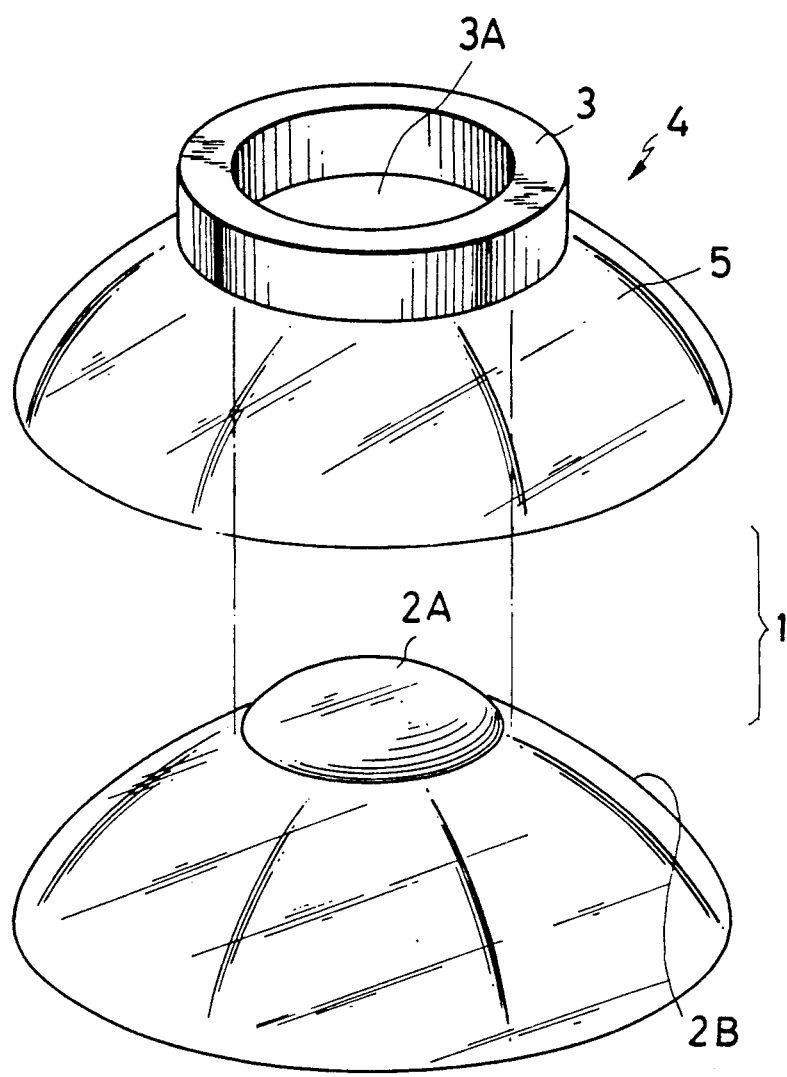
FIG. 1 shows a perspective view of a disintegrated state of an auxiliary instrument for examination of eyes according a first embodiment of this invention.
Figure 2:
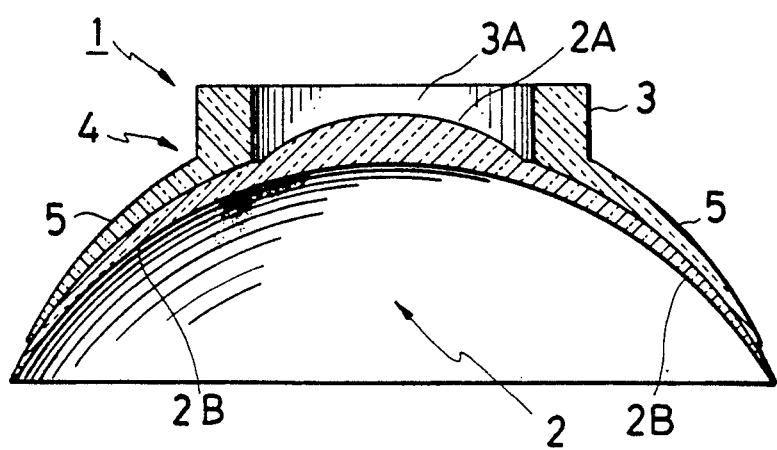
FIG. 2 is a sectional view of the auxiliary instrument shown in FIG. 1, which is being assembled.

As shown in FIGS. 1 and 2, an auxiliary instrument for examining eyes 1 comprises a contact lens portion 2, and an overlaying lens portion 4 having a guiding wall portion 3 and adapted to be assembled with the contact lens portion 2.

The inner surface of the contact lens portion 2 is made into a spherical shape in conformity with the spherical shape of the surface of cornea of an eyeball. Namely, this contact lens 2 comprises a circumferential surface portion 2B having a spherical surface, and an examination surface portion 2A which is disposed at the central portion of the contact lens so as to correspond to the position of pupil and formed into a convex lens whose outer curvature is similar to that of a pupil. Thus, this contact lens 2 may be a soft contact lens (or a soft contact lens made of hydroxymethylmethacrylate).

The examination surface portion 2A may preferably be made to have a refractive index similar to that of the cornea of an eyeball. For example, the examination surface portion 2A may be designed to have the following features: DK=8.5; water content =38%; thickness at the central portion =0.5 mm; and an optical diameter =5.0 mm.

The overlaying lens portion 4 is made of the same material as that of the contact lens portion 2 and is provided with a guiding wall 3.

This guiding wall 3 is of a cylindrical shape having both ends thereof made open. A hollow window 3A of the overlaying lens portion 4 is designed to have a diameter (in this example, 5.5 mm) which is slightly larger than that of the examination surface portion 2A of the contact lens.

The bottom surface 5 of the overlaying lens portion 4 is formed into a spherical shape which conforms to the top surface 2B (excluding the examination surface portion 2A) of the contact lens portion 2 so as to be hermetically contacted therewith.

The contact lens portion 2 may be prepared in several different shapes in order to correspond to a particular outer shape of the eyeball of an individual patient, thereby making it possible to select an optimum shape of the contact lens portion 2 for any patient.

The contact lens portion 2 may be substituted by a contact lens which has been worn by a patient himself.

When diseased part of an eye of a patient is to be photographed by means of a specular microscope by using an auxiliary instrument having the above construction, the contact lens portion 2 is first fitted to a predetermined portion of the cornea of an eyeball of a patient in the same manner as conducted in wearing an ordinary soft contact lens.

Then, the overlaying lens portion 4 is overlaid on the contact lens portion 2. In this case, since the overlaying lens portion 4 is made of the same material as that of the contact lens portion 2, the overlaying lens portion 4 can be hermetically fitted to the contact lens portion 2 by merely wetting the surface of the contact lens portion in prior to overlaying the overlaying lens portion 4.

Specifically, the overlaying lens portion 4 is positioned in such a manner that the examination surface portion 2A of the contact lens portion 2 is fitted in the hollow window 3A of the guiding wall 3 so that the guiding wall 3 is in coaxial relation with the center of the examination surface portion 2A, and at the same time the bottom surface 5 of the overlaying lens portion 4 is hermetically set on the top surface 2B of the contact lens portion 2.

In this manner, the auxiliary instrument 1 of this invention can be fitted in an eye of a patient.

Then, the distal end of cone lens (not shown) of a specular microscope is inserted into the hollow window 3A of the guiding wall 3. Thereafter, a photograph of the diseased part of a patient's eye can be taken through the examination surface portion 2A, while contacting the cone lens to the examination surface portion 2A, in the same manner as performed in the conventional method of contacting the cone lens to a position of a pupil.

Since the examination surface portion 2A also serves as a lens when contacted with outer surface of the cone lens, the examination surface portion 2A should be finished as a lens of high precision.

It has become possible to take a photograph in a stabilized state, since the outer circumferential wall of the cone lens is contacted with the inner surface of the guiding wall 3 and kept retained at a predetermined set position thereby preventing the cone lens from being shaken.

After finishing the examination, the contact lens portion 2 can be detached from an eye together with the overlaying lens portion 4.

In order to accurately align the overlaying lens portion 4 with the contact lens portion 2, it may be convenient to provide at a contacting position of them an engaging means such as a projection or a depression.

Figure 3:
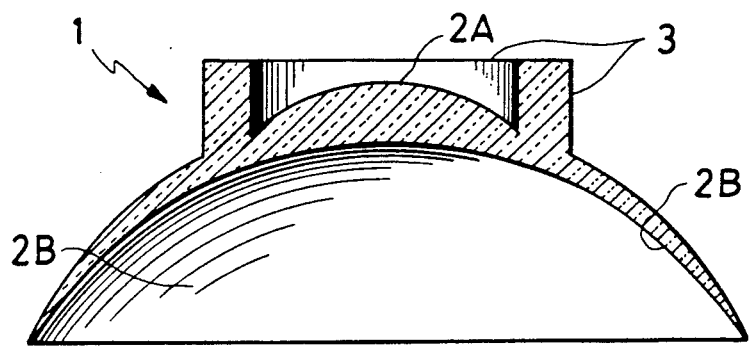
FIG. 3 is a sectional view of an auxiliary instrument for examination of eyes according to a second embodiment of this invention;, and FIG. 4(a&b) are a plan view of an auxiliary instrument for the examination of eyes according to still another embodiment of this invention.

FIG. 3 shows a second embodiment of the auxiliary instrument for examining eyes according to this invention.

This auxiliary instrument 1 comprises a contact lens portion 2 which is integrally provided with a guiding wall 3 protruding from the circumference of an examination surface portion 2A. Therefore, there is no need to prepare the contact lens portion 2 and the overlaying lens portion separately, and therefore the construction of the auxiliary instrument is rather simple as a whole.

In this case, since the guiding portion 3 can be mounted to an eye in simultaneous with the mounting operation of the contact lens portion 2, the mounting operation of the auxiliary instrument becomes more simple as compared with the first embodiment.

Other constructions and operation of this second embodiment are the same as those of the first embodiment, so that explanations of them are omitted by simply putting the same reference numerals to the same portions as those of the first embodiment.

The shape of the guiding wall 3 of the auxiliary instrument 1 is not restricted to that of cylindrical shape as shown in the above embodiments, but may take any other shapes as long as merit of this invention is not hindered.

Figure 4A:
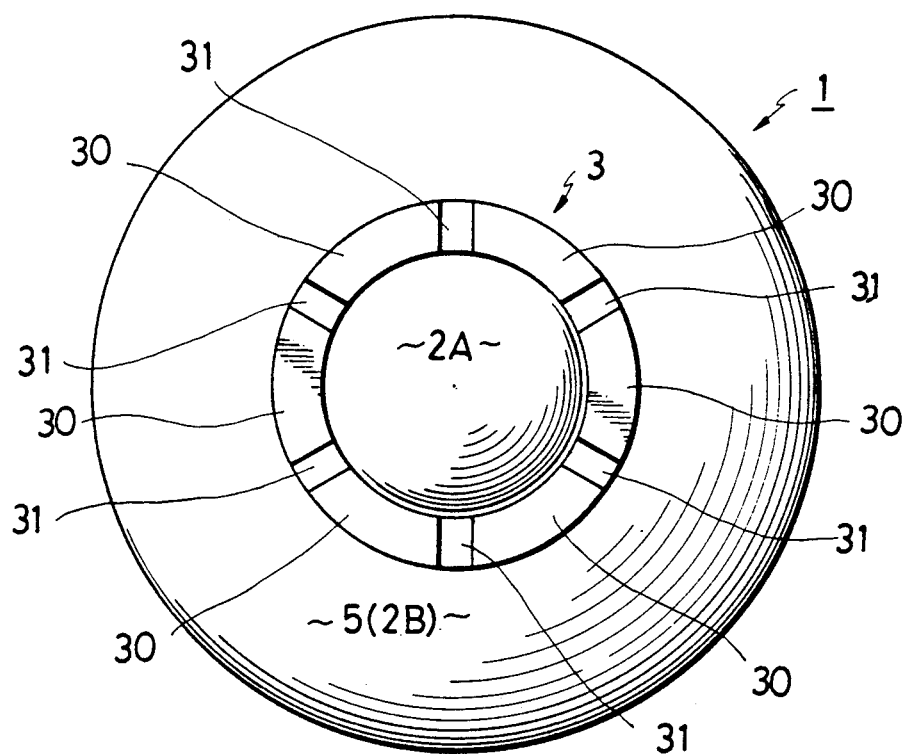
Figure 4B:
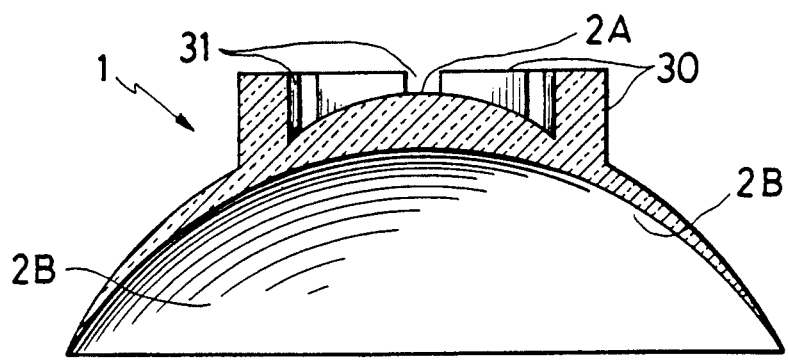

For example, in the guiding wall 3 shown in FIG. 4, a plurality of slits 31 are formed at an equal interval in the top surface of the cylinder, thereby dividing the cylinder into a plurality of protruding pieces 30.

With this structure, it is possible to easily bend the protruding pieces 30 and to retain a tip portion of an examining instrument therein, even if the tip portion is slightly larger than the inner diameter of the guiding wall, or different in outer shape from that of the inner shape of the guiding wall 3.

Likewise, the guide wall 3 may consist of a plurality of protruding pieces having any desired shape, and kept apart at an equal distance to surround the circumference of the examination surface portion 2A of the contact lens portion 2.

A rib and the like (not shown) for locking the tip portion of an examining instrument may be provided to project from the inner top portion of the guiding wall 3.

In the above embodiments, an employment of a cone lens a specular microscope is discussed as an example of an examining instrument. However, it is also possible according to this invention to utilize the auxiliary instrument in combination with other examining instrument.

For example, the auxiliary instrument of this invention may be employed in combination with a tonometer. In this case, the examination surface portion 2A is not required to be of a lens, and may preferably be formed into a portion of uniform thickness in order to accurately measure the intraocular tension.

Moreover, the shape and structure of the examination surface portion surrounded by a guiding wall according to this invention is not restricted to the embodiments as explained above, but may be modified into any suitable shape or structure in conformity to the object of the examination as well as to the type of the examining instrument. For example, a through hole communicating with the surface of an eyeball may be provided to the examining surface portion.

Other modifications are also possible as far as the merit of this invention is not substantially hindered.

According to this invention, since a guiding wall is protrusively disposed to surround the circumference of the examination surface portion of the contact lens portion, the positioning of the tip portion of an examining instrument can be easily achieved by merely inserting the tip portion into the hollow window inside the guiding wall, and the examining operation can be easily conducted within a relatively short period of time by keeping the tip portion retained within the guiding wall.

Further, since an examining instrument is no more directly contacted with ectocornea by the use of this auxiliary instrument in contrast to the conventional method, there is no possibility of locally pressing an eyeball with the examining instrument, of injuring the ectocornea, or of being infected through the examining instrument. Therefore, medical safety during the examination of eyes can be greatly improved.

When the examining part of eyes of a patient is of the patient pupil, the field of patient's view is suitably restricted by the presence of the guiding wall protrusively surrounding the contacted portion of the examining instrument, thereby making it easy to open the pupil during a photographing operation, and promoting the efficiency of the eye-examination.

What is claimed is:

1. An auxiliary instrument for examining an eye comprising:
   a contact lens having a spherical surface portion for contacting the surface of the cornea of an eyeball;
   an examination member including a spherical surface portion for overlying and engaging a portion of said contact lens, said examination member including a central opening and wall means surrounding said central opening, said surface portion of said examination member having a concave side and a convex side with said wall means protruding from said convex side a selected distance.

2. An auxiliary instrument according to claim 1, wherein said examination member is formed of a convex lens having an external curvature similar to that of a pupil.

3. An auxiliary instrument according to claim 11, wherein said examination member has a refractive index similar to that of the cornea of eyeball.

4. An auxiliary instrument according to claim 1, wherein said examination member is circular in shape and disposed at the central portion of said contact lens, which is in alignment with a position of a pupil.

5. An auxiliary instrument according to claim 1, wherein said wall is cylindrical in shape.

* * * * *